US00PP28982P2

(12) United States Plant Patent
van Langen

(10) Patent No.: US PP28,982 P2
(45) Date of Patent: Feb. 20, 2018

(54) ***ALOE* PLANT NAMED 'AMIAL1605'**

(50) Latin Name: *Aloe aristata*
Varietal Denomination: AMIAL1605

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,564

(22) Filed: Jan. 30, 2017

(30) Foreign Application Priority Data

Aug. 11, 2016 (QZ) ..... PBR 2016/1965

(51) Int. Cl.
*A01H 5/12* (2006.01)

(52) U.S. Cl.
USPC ..... Plt./373

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Aloe aristata* cultivar named 'AMIAL1605' which is characterized by a flattened globular plant shape, a short plant height, ovate foliage with an acute to broadly acute apex, and a short caudate tip dark green mature foliage with a moderately dense occurrence of prominent white papillae on both the adaxial and abaxial surfaces, as well as the stability of these characteristics from generation to generation.

4 Drawing Sheets

Latin name of the genus and species: The Latin name of the genus and species of the novel variety disclosed herein is *Aloe aristata.*

Variety denomination: The inventive variety of *Aloe* disclosed herein has been given the variety denomination 'AMIAL1605'.

CROSS REFERENCE TO RELATED APPLICATIONS

This application claims priority to the Community Plant Variety Rights application number 2015/1965, filed Aug. 11, 2016, which is herein incorporated by reference.

BACKGROUND OF THE INVENTION

Parentage: 'AMIAL1605' originated as a naturally occurring, whole-plant mutation of the species *Aloe aristata* (not a named variety or cultivar, unpatented). In February of 2012 the inventor discovered the mutation at a commercial greenhouse in Heerhugowaard, the Netherlands, growing amongst a crop of the species *Aloe aristata*. The mutation was noted for its prominent white papillae on the foliage and was subsequently isolated for further evaluation in order to confirm the distinctness and stability of the characteristics first observed. Upon confirmation of distinctness and stability, 'AMIAL1605' was selected for commercialization in the summer of 2014.

Asexual Reproduction: Asexual reproduction of the new cultivar 'AMIAL1605', by way of rooting leaf cuttings, was first initiated in the summer of 2015 at the inventor's commercial greenhouse in Heerhugowaard, The Netherlands. The claimed plant has since been asexually propagated by way of meristematic tissue culture propagation.

Through four subsequent generations, the unique features of this cultivar have proven to be stable and true to type.

SUMMARY OF THE INVENTION

The cultivar 'AMIAL1605' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1605'. These characteristics in combination distinguish 'AMIAL1605' as a new and distinct *Aloe aristata* cultivar:

1. 'AMIAL1605' exhibits thick succulent foliage, arranged in a basal rosette, with a flattened globular profile and a shorter overall plant height; and
2. 'AMIAL1605' exhibits foliage that is slightly curved upward, with innermost whorls of foliage appearing to be more loosely held; and
3. 'AMIAL1605' exhibits ovate foliage with dentate leaf margins, an acute to broadly acute apex, and a short caudate tip; and
4. 'AMIAL1605' exhibits dark green mature foliage with a moderately dense occurrence of prominent white papillae on both the adaxial and abaxial surfaces.

BOTANICAL DESCRIPTION OF THE PLANT

Figure 1:
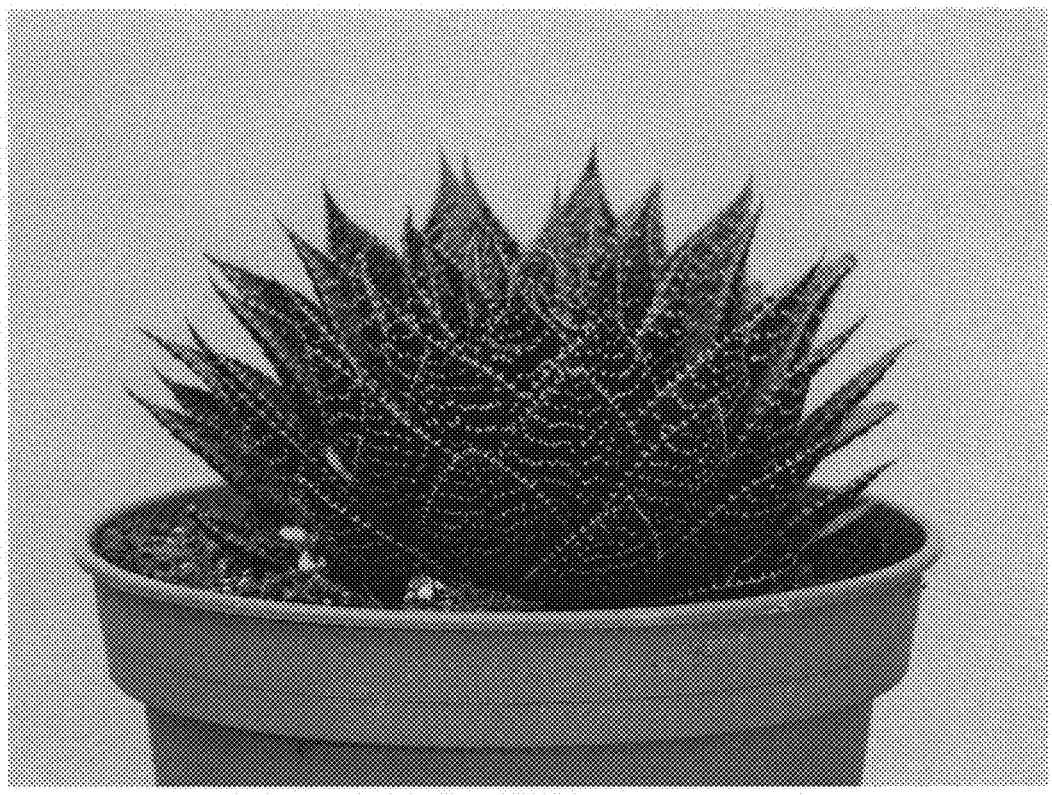
FIG. 1 illustrates, as nearly true as it is reasonably possible to make the same in color photographs of this type, an exemplary plant of 'AMIAL1605' grown in a commercial greenhouse in Heerhugowaard, The Netherlands. This plant is approximately 9 months old, shown planted in a 15 cm container.
Figure 2:
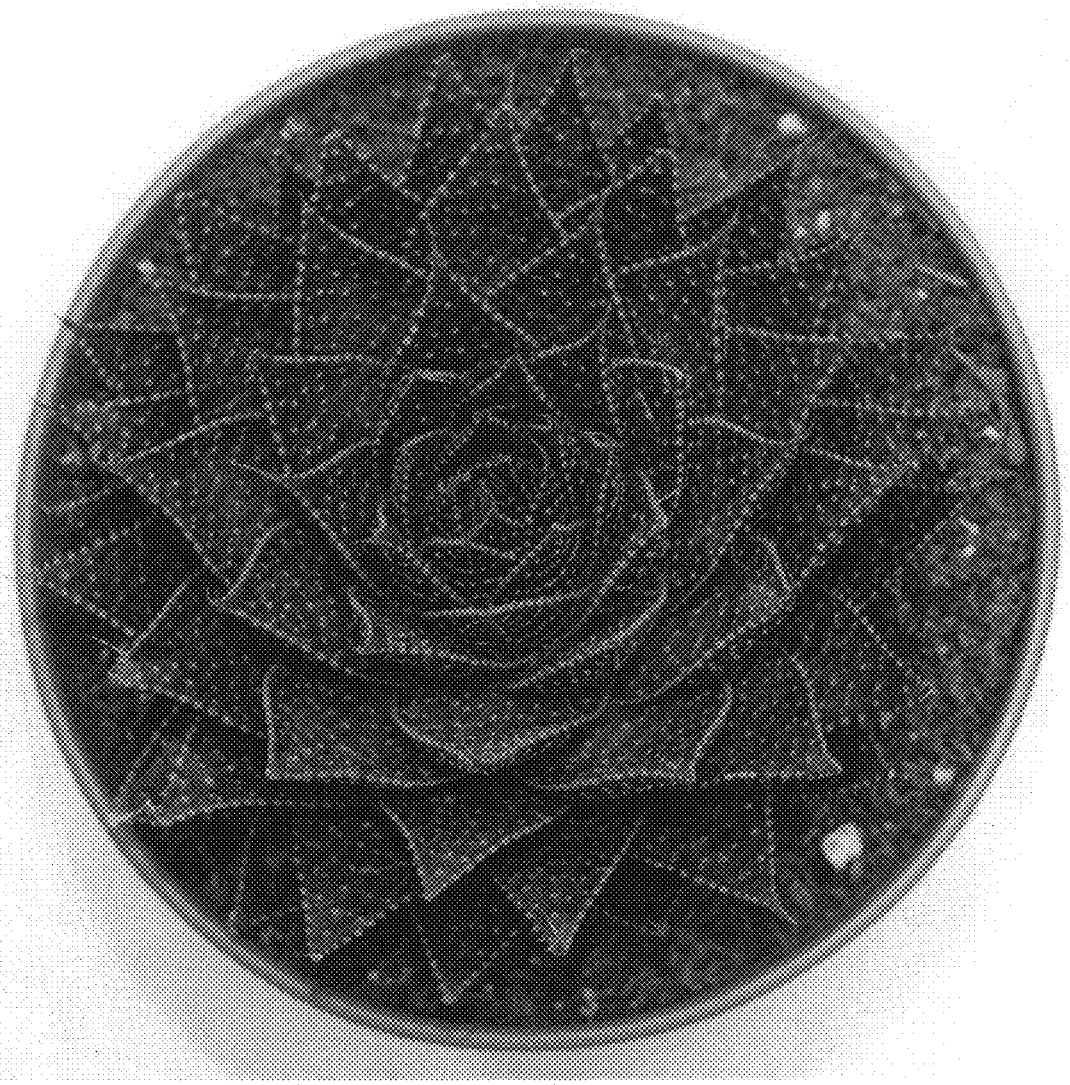
FIG. 2 illustrates, as nearly true as it is reasonably possible to make the same in color photographs of this type, the typical foliage arrangement of 'AMIAL1605'.
Figure 3:
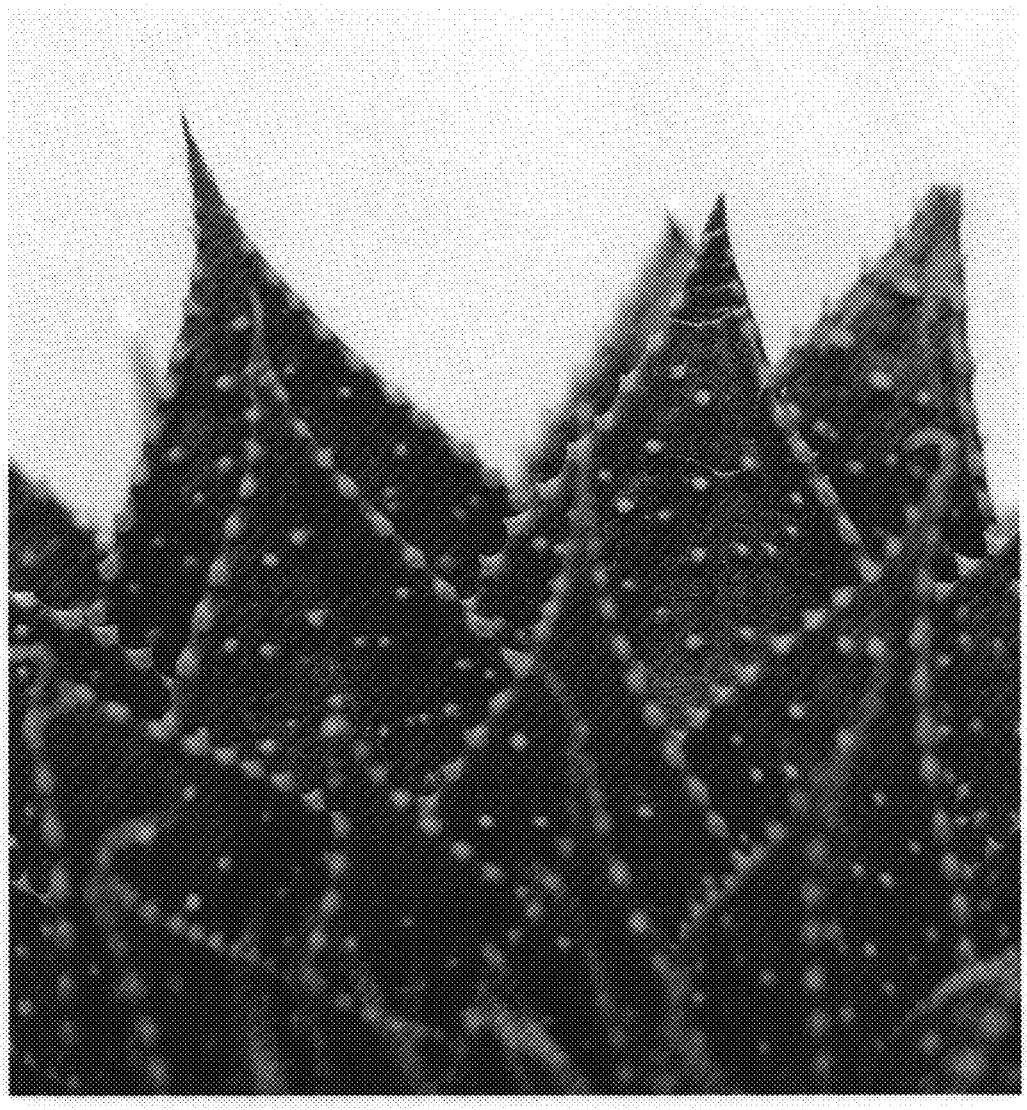
FIG. 3 illustrates, as nearly true as it is reasonably possible to make the same in color photographs of this type, the adaxial surface of the mature foliage 'AMIAL1605'.
Figure 4:
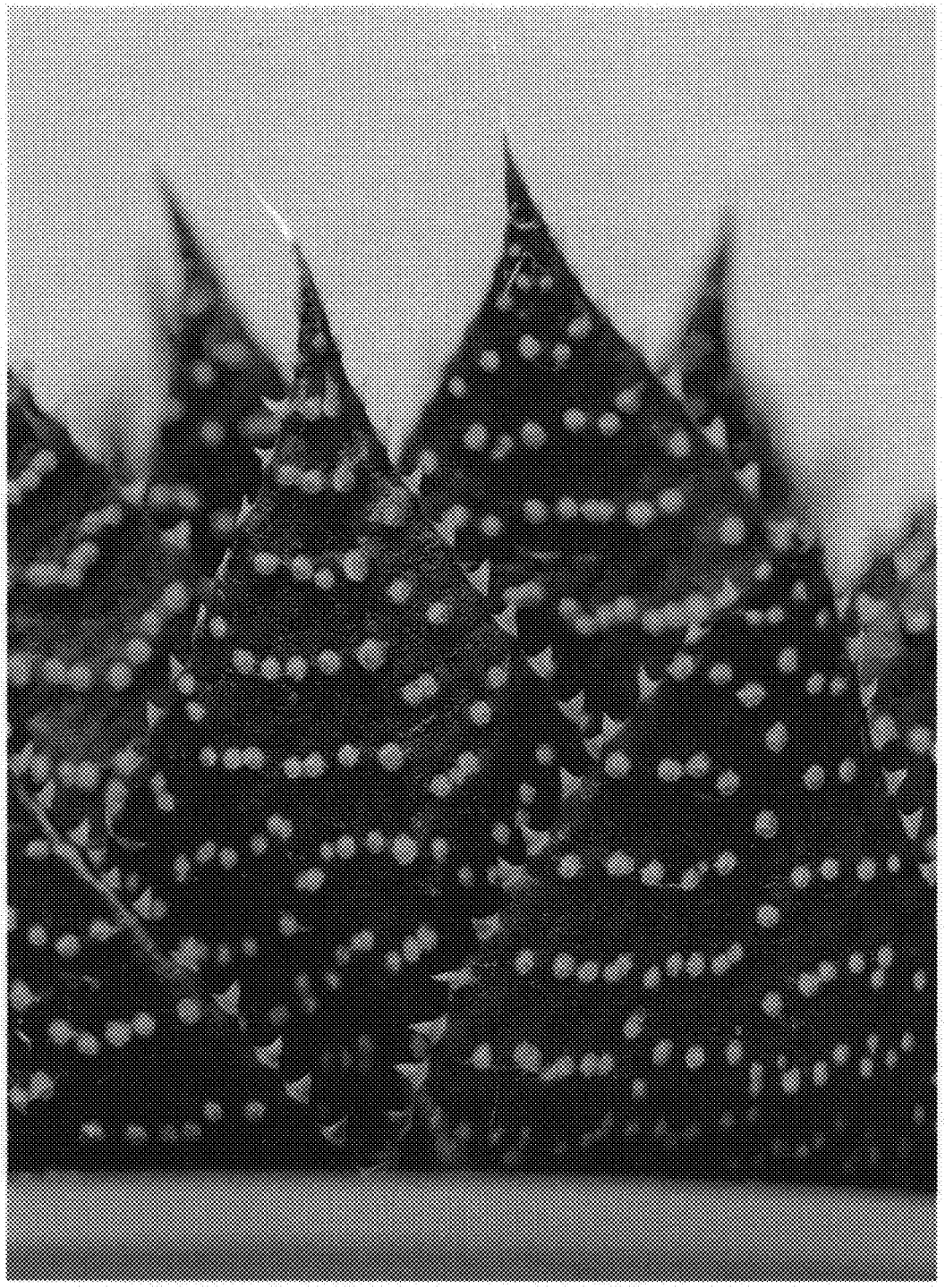
FIG. 4 illustrates, as nearly true as it is reasonably possible to make the same in color photographs of this type, the abaxial surface of the mature foliage 'AMIAL1605'.

The following observations and measurements made in October of 2016 describe averages from a sample set of six specimens of 9 months old 'AMIAL1605' plants grown in 15 cm nursery containers at commercial greenhouse in Heerhugowaard, The Netherlands. Plants were produced using conventional greenhouse production protocols for *Aloe* which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIAL1605' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1605' and a comparison with the parent and closest known comparator is provided below.

Plant description:

*Growth habit*.—Succulent perennial with foliage growing in a non-branched basal rosette.

*Plant shape*.—Flattened globular.

*Height from soil level to top of foliar plane*.—8.5 cm.

*Plant spread*.—Average of 13.7 cm.

*Growth rate*.—Low to moderate.

*Plant vigor*.—Low to moderate.

*Propagation*.—Type — Leaf cuttings. Time to initiate rooting — Approximately 28 to 35 days at 18 degrees Celsius. Crop time — Approximately 15 to 20 weeks to produce a marketable plant in a 7 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 90 leaves per rosette.

*Shape*.—Thick, succulent leaves which are ovate to narrow ovate.

*Dimensions*.—6.8 cm long, 2.9 cm wide, and 0.7 cm thick, on average.

*Aspect*.—Slightly concave.

*Attitude*.—Slightly curved upward.

*Apex*.—Acute to broadly acute with a caudate tip.

*Base*.—Broad cuneate.

*Margin*.—Dentate; not undulated or lobed.

*Texture, adaxial surface*.—Glabrous and moderately covered with papillae, each approximately 1.0 mm high and 1.0 mm in diameter.

*Texture, abaxial surface*.—Glabrous with papillae more or less arranged in axial rows; papilla are approximately 1.0 mm high and 1.0 mm in diameter.

*Luster, adaxial surface*.—Slightly to moderately glossy.

*Luster, abaxial surface*.—Slightly glossy.

*Color*.—Juvenile foliage, adaxial surface — Green, nearest to RHS 139A, and fading to yellow-green towards the base, nearest to RHS N144D; leaf moderately covered with papillae which are colored greyed-green, in between RHS 191D and 192D. Juvenile foliage, abaxial surface — In between green, RHS NN137A, and yellow-green, RHS 147A; fading to yellow-green towards the base, in between RHS 144A and 144B; leaf moderately to densely covered with papillae which are colored greyed-green, nearest to RHS 192D. Mature foliage, adaxial surface — In between green, RHS NN137A, and yellow-green, RHS 147A; fading to yellow-green towards the base, nearest to RHS 147D, and suffused with greyed-green, RHS 194C; outermost tip of the apex is greyed-red, in between RHS 180C and 180D; leaf moderately covered with papillae which are colored greyed-green, in between RHS 191D and 192D. Mature foliage, abaxial surface — In between green, RHS NN137A, and yellow-green, RHS 147A; fading lighter towards the base, nearest to RHS 147C, and suffused with greyed-green, nearest to RHS 192C; outermost tip of the apex is greyed-red, in between RHS 180C and 180D; leaf moderately to densely covered with papillae, more or less arranged in axial rows, which are colored greyed-green, in between RHS 191D and 192D.

*Venation*.—No venation is visible.

*Petiole*.—No petiole; leaves are sessile.

Inflorescence: No flowering has been observed to date.

COMPARISONS WITH THE PARENT PLANT

Plants of the new cultivar 'AMIAL1605' differ from the parent, unnamed plant of *Aloe aristata*, in the following characteristics described in Table 1 below.

TABLE 1

| Characteristic | 'AMIAL1605' | Unnamed plant of *Aloe aristata* |
|---|---|---|
| Abundance of foliage. | Fewer leaves in the rosette. | More leaves in the rosette. |
| Leaf apex. | Acute to broadly acute with shorter caudate tip. | Narrowly acute with a caudate tip. |
| Leaf width. | Approximately 1.5 times wider than the parent. | Narrower than 'AMIAL1605'. |
| General coloration of mature foliage. | Dark green. | Green to yellow green and suffused with greyed-green. |

COMPARISONS WITH THE CLOSEST KNOWN COMPARATOR

Plants of the new cultivar 'AMIAL1605' differ from the commercial variety, *Aloe* 'Green Pearl' (not patented in the United States; European Union CPVO grant EU18402), in the following characteristics described in Table 2 below.

TABLE 2

| Characteristic | 'AMIAL1605' | 'Green Pearl' |
|---|---|---|
| Growth habit. | Basal rosette with innermost whorls of juvenile foliage appearing to be more loosely held than those of 'Green Pearl'. | Basal rosette with innermost whorls of juvenile foliage appearing to be more tightly held. |
| Leaf attitude, juvenile foliage. | Foliage has a more relaxed attitude when compared to 'Green Pearl'. | Erect. |
| Leaf thickness. | Thicker than the 'Green Pearl'. | Thinner than 'AMIAL1605'. |
| Mature foliage; occurrence of papillae. | Prominent white papillae. | Nearly void of papillae. |

That which is claimed is:

1. A new and distinct variety of *Aloe aristata* plant named 'AMIAL1605', substantially as described and illustrated herein.

* * * * *